US006358697B2

(12) United States Patent
Rothenberg et al.

(10) Patent No.: US 6,358,697 B2
(45) Date of Patent: *Mar. 19, 2002

(54) INTRACELLULAR PHARMACEUTICAL TARGETING

(75) Inventors: Marc E. Rothenberg; Nives Zimmermann, both of Cincinnati, OH (US)

(73) Assignee: Children's Hospital Medical Center, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/296,071

(22) Filed: Apr. 21, 1999

(51) Int. Cl.[7] ..................... G01N 33/53; G01N 33/566; A61K 38/19
(52) U.S. Cl. ..................... 435/7.21; 435/7.1; 435/7.2; 435/7.26; 435/7.9; 424/85.1; 514/2; 514/8; 514/12; 514/885
(58) Field of Search .................. 435/7.1, 7.2, 7.21, 435/7.24, 7.9; 424/85.1; 514/2, 8, 12, 885

(56) References Cited

U.S. PATENT DOCUMENTS

| | | |
|---|---|---|
| 5,426,029 A | 6/1995 | Rittershaus et al. ....... 435/7.21 |
| 5,595,897 A | 1/1997 | Midoux et al. .......... 435/172.3 |
| 5,656,724 A | 8/1997 | Daly et al. .................. 530/324 |
| 5,789,539 A | 8/1998 | Daly et al. .................. 530/324 |
| 5,792,444 A | 8/1998 | Fischman et al. .......... 424/1.69 |
| 5,861,475 A | 1/1999 | Cooper, Jr. ................. 530/300 |
| 5,874,211 A | 2/1999 | Bandman et al. .............. 435/6 |

FOREIGN PATENT DOCUMENTS

| | | |
|---|---|---|
| WO | WO 96/22371 | 7/1996 |
| WO | WO 97/00960 | 1/1997 |
| WO | WO 97/41154 | 11/1997 |
| WO | WO 98/11218 | 3/1998 |
| WO | WO 00/04926 | 2/2000 |

OTHER PUBLICATIONS

Amara et al. HIV Coreceptor Downregulation as Antiviral Principle: SDF–1 alpha–dependent Internaziation of the Chemokine Receptor CXCR–4 Contributes to Inhibition of HIV Replication. Journal of Experimental Medicine, vol. 186, No. 6, pp. 139–146, Jul. 1997.*

Kane et al. Prostaglandins, vol. 50, pp. 1–18, Jul. 1995.*

E.A. Garcia–Zepeda et al., Human Monocyte Chemoattractant Protein (MCP)–4 Is a Novel CC Chemokine with Activities on Monocytes, Eosinophils, and Basophils Induced in Allergic and Nonallergic Inflammation That Signals Through the CC Chemokine Receptors (CCR)–2 and –3, The Journal of Immunology, 1996, 157:5613–5626.

N. Zimmerman et al., Molecular Analysis of CCR–3 Events in Eosinophilic Cells, The Journal of Immunology, 2000, 164:1055–1064.

N. Zimmerman et al., CC Chemokine Receptor–3 Undergoes Prolonged Ligand–induced Internalization, J. Biol. Chem., 1999, 274(18): 12611–12618.

G. J. Gleich et al., The Eosinophilic Leukoyete: Structure and Function, Adv. Immunol. 39, 177–253 (1986).

P.F. Weller, The Immunobiology of Eosinophils, N. Engl. J. Med. 324, 1110–1118 (Apr. 18, 1991).

M.E. Rothenberg, Eosinophilia, N. Engl. J. Med. 338, 1592–1600 (May 28, 1998).

P.J. Jose et al., Eotaxin: A Potent Eosinophil Chemoattractant Cytokine Detected in a Guinea Pig Model of Allergic Airways Inflammation, J. Exp. Med. 179, 881–887 (Mar. 1994).

A.D. Luster and M.E. Rothenberg, Role of the monocyte chemoattractant protein and eotaxin subfamily of chemokines in allergic inflammation, J. Leukocyte Biol. 62, 620–633 (Nov. 1997).

M. Baggiolini et al., Interleukin–8 and Related Chemotactic Cytokines—CXC and CC Chemokines, Adv. Immunol. 55, 97–179 (1994).

B.J. Rollins, Chemokines, Blood 90, 909–928 (Aug. 1, 1997).

A.D. Luster, Chemokines—Chemotactic Cystokines That Mediate Inflammation, N. Engl. J. Med. 338, 436–445 (Feb. 12, 1998).

P.M. Murphy, The Molecular Biology of Leukocyte Chemoattractant Receptors, Annu. Rev. Immunol. 12, 593–633 (1994).

C. Gerard and N.P. Gerard, The pro–inflammatory seven–transmembrane segment receptors of the leukocyte, Curr. Opin. Immunol. 6, 140–145 (1994).

P. Bates, Chemokine Receptors and HIV–1: An Attractive Pair?, Cell 86, 1–3 (Jul. 12, 1996).

C. Combadiere et al., Cloning and Functional Expression of a Human Eosinophil CC Chemokine Receptor, J. Biol. Chem 270, 16491–16494 (Jul. 14, 1995); Correction J. Biol. Chem. 271, 111034 (1996).

(List continued on next page.)

Primary Examiner—Christine J. Saoud
Assistant Examiner—Fozia Hamud
(74) Attorney, Agent, or Firm—Wood, Herron & Evans, LLP

(57) ABSTRACT

A method and composition to target compounds into cells such as eosinophils. A ligand for a CCR-3 eosinophil surface receptor is provided under conditions to bind to the receptor and cause internalization of the ligand-CCR-3 complex. A compound, such as a drug in an active or inactive form, may be bound to the ligand and delivered to an intracellular site of the cell where it may subsequently become activated. The methods and compositions may be used to treat a variety of eosinophil-mediated disorders, for example, allergies.

25 Claims, 5 Drawing Sheets

OTHER PUBLICATIONS

B.L. Daugherty et al., Cloning, Expression, and Characterization of the Human Eosinophil Eotaxin Receptor, J. Exp. Med. 183, 2349–2354 (May 1996).

P.D. Ponath et al., Molecular Cloning and Characterization of a Human Eotaxin Receptor Expressed Selectively on Eosinophils, J. Exp. Med. 183, 2437–2448 (Jun. 1996).

F. Sallusto et al., Selective Expression of the Eotaxin Receptor CCR3 by Human T Helper 2 Cells, Science 277, 2005–2007 (Sep. 26, 1997).

M. Uguccioni et al., High Expression of the Chemokine Receptor CCR3 in Human Blood Basophils, J. Clin. Invest. 100, 1137–1143 (Sep. 1997).

J.A. Gonzalo et al., Eosinophil Recruitment to the Lung in a Murine Model of Allergic Inflammation, J. Clin. Invest. 98, 2332,2345 (Nov. 1996).

A.A. Humbles et al., Kinetics of Eotaxin Generation and Its Relationship to Eosinophil Accumulation in Allergic Airways Disease: Analysis in a Guinea Pig Model In Vivo, J. Exp. Med. 186, 601–612 (Aug. 18, 1997).

B. Lamkhioued et al., Increased Expression of Eotaxin in Bronchoalveolar Lavage and Airways of Asthmatics Contributes to the Chemotaxis of Eosinophils to the Site of Inflammation, J. Immunol. 159, 4593–4601 (1997).

M. M. Teixeira et al., Chemokine–induced Eosinophil Recruitment, J. Clin. Invest. 100, 1657–1666 (Oct. 1997).

M.E. Rothenberg et al., Targeted Disruption of the Chemokine Eotaxin Partially Reduces Antigen–induced Tissue Eosinophilia, J. Exp. Med. 185, 785–790 (Feb. 17, 1997).

A.N. Matthews et al., Eotaxin is required for the baseline level of tissue eosinophils, Proc. Natl. Acad. Sci. U.S.A. 95, 6273–6278 (May 1998).

S.K. Bohm et al., Regulatory mechanisms that modulate signalling by G–protein–coupled receptors, Biochem. J. 322, 1–18 (1997).

R.J. Uhing et al., Differential Regulation of cAMP by Endogenous Versus Transfected Formylpeptide Chemoattractant Receptors: Implications for Gi–Coupled Receptor Signaling, Biochem. Biophys. Res. Commun. 183, 1033–1039 (Mar. 31, 1992).

T.T. Hansel et al., An improved immunomagnetic procedure for the isolation of highly purified human blood eosinophils, J. Immunol. Methods 145, 105–110 (1991).

H.K. Deng et al., Identification of a major co–receptor for primary isolates of HIV–1, Nature 381, 661–666 (Jun. 20, 1996).

N.R. Landau and D.R. Littman, Packaging System for Rapid Production of Murine Leukemia Virus Vectors with Variable Tropism, J. Virol. 66, 5110–5113 (Aug. 1992).

A.K. Samanta et al., Interleukin 8 (Monocyte–derived Neutrophil Chemotactic Factor) Dynamically Regulates Its Own Receptor Expression on Human Neutrophils, J. Biol. Chem. 265, 183–189 (Jan. 5, 1990).

A. Chuntharapai and K. Jin Kim, Regulation of the Express of IL–8 Receptor A/B by IL–8: Possible Functions of Each Receptor, J. Immunol. 155, 2587–2594 (1995).

S. Eskelinen et al., Coated endosomal vesicles: sorting and recycling compartment for transferrin in BHK cells, Eur. J. Cell Biol. 56, 210–222 (1991).

K. Tenscher et al., Recombinant Human Eotaxin Induces Oxygen Radical Production, Ca2+–Mobilization, Actin Reorganization, and CD11b Upregulation in Human Eosinophils Via a Pertussis Toxin–Sensitive Heterotrimeric Guanine Nucleotide–Binding Protein, Blood 88, 3195–3199 (Oct. 15, 1996).

M. Mack et al., Aminooxypentane–RANTES Induces CCR5 Internalization but Inhibits Recycling: A Novel Inhibitory Mechanism of HIV Infectivity, J. Exp. Med. 187, 1215–1224 (Apr. 20, 1998).

I. Clark–Lewis et al., Structure–Activity Relationships of Interleukin–8 Determined Using Chemically Synthesized Analogs, J. Biol. Chem. 266, 23128–23134 (Dec. 5, 1991).

A. Amara et al., HIV Coreceptor Downregulation as Antiviral Principle: SDF–1α–dependent Internalization of the Chemokine Receptor CXCR4 Contributes to Inhibition of HIV Replication, J. Exp. Med. 186, 139–146 (Jul. 7, 1997).

R. Förster et al., Intracellular and Surface Expression of the HIV–1 Coreceptor CXCR4/Fusin on Various Leukocyte Subsets: Rapid Internalization and Recycling Upon Activation, J. Immunol. 160, 1522–1531 (1998).

S. G. Mueller et al., Activation of Protein Kinase C Enhances the Phosphorylation of the Type B Interluekin–8 Receptor and Stimulates Its Degradation in Non–hematopoietic Cells, J. Biol. Chem. 270, 10439–10448 (May 5, 1995).

R. Solari et al., Receptor–mediated Endocytosis of CC–chemokines, J. Biol. Chem. 272, 9617–9620 (Apr. 11, 1997).

C. Franci et al., Phosphorylation by a G Protein–Coupled Kinase Inhibits Signaling and Promotes Internalization of the Monocyte Chemoattractant Protein–1 Receptor, J. Immunol. 157, 5606–5612 (1996).

I. Mellman, Endocytosis and Molecular Sorting, Annu. Rev. Cell Dev. Biol. 12, 575–625 (1996).

I. Aramori et al., Molecular mechanism of desensitization of the chemokine receptor CCR–5: receptor signaling and internalization are dissociable from its role as an HIV–1 co–receptor, The EMBO Journal 16, 4606–4616 (1997).

H. Choe et al., The β–Chemokine Receptors CCR3 and CCR5 Facilitate Infection by Primary HIV–1 Isolates, Cell 85, 1135–1148 (Jun. 28, 1996).

\* cited by examiner

INTRACELLULAR PHARMACEUTICAL TARGETING

The U.S. Government has a paid-up license in this invention and the right in limited circumstances to require the patent owner to license others on reasonable terms as provided for by the terms of Grant No. R01-AI42242-02 awarded by the National Institutes of Health.

FIELD OF THE INVENTION

The invention relates to targeted drug therapy in general, and to eosinophil targeting in particular.

BACKGROUND OF THE INVENTION

Eosinophils are one type of granulocytic leukocyte (white blood cell) or granulocyte that normally appear in the peripheral blood at a concentration of about 1–3% of total leukocytes. Their presence in tissues is normally primarily restricted to the gastrointestinal mucosa. In various disease states, eosinophils appear in increased numbers in the peripheral blood and/or tissues, a condition termed eosinophilia and described in Rothenberg, Eosinophilia, N. Engl. J. Med. 338, 1592–1600 (1998). Eosinophil accumulation in tissues may cause potent pro-inflammatory effects in many diseases. Eosinophilia occurs in various diseases including allergic disorders such as allergic rhinitis, asthma, and eczema, chronic inflammatory disorders such as inflammatory bowel disease, and specific syndromes such as eosinophilic gastroenteritis, eosinophilic colitis, eosinophilic cellulitis and eosinophilic fasciitis, as well as parasitic infections and certain types of malignancies.

Numerous pharmaceutical agents, known to inhibit eosinophil function, are used to treat a variety of eosinophil-related diseases. However, none of these agents have a mechanism of action that is directed specifically to eosinophils. For example, glucocorticoids are the most common treatment for allergic disorders, but glucocorticoids are nonspecific for eosinophils in addition to being highly toxic. Another type of non-specific inhibition of eosinophil function is by administration of the non-specific adhesion molecule blockers such as very-late-antigen 4 (VLA-4) inhibitors. Interleukin-5 (IL-5), a chief eosinophil growth factor, is also under evaluation as a compound to target for the purpose of specifically inhibiting eosinophilia. In animal studies, blocking IL-5 by administering a humanized monoclonal antibody against IL-5 has been demonstrated to be highly effective in blocking eosinophil-mediated diseases such as asthma. Blocking IL-5 action would, therefore, likely reduce the symptoms of asthma. However, no clinically feasible small molecule inhibitors have been identified that inhibit IL-5. The only current approach to IL-5 targeting is by administering neutralizing antibody.

A therapeutic agent that could specifically target eosinophil function and trafficking would therefore be desirable. Such an agent could be used for treatment of the wide variety of eosinophil-mediated conditions that are known. For example, pediatric asthma is an eosinophil-mediated condition whose incidence is on the rise and is now the chief diagnosis responsible for pediatric hospital admissions. Alleviation of pediatric asthma by an eosinophil-targeting agent, along with the spectrum of other eosinophil-mediated conditions, would be of tremendous benefit.

SUMMARY OF THE INVENTION

The invention is directed to a method for intracellular targeting. A ligand for a cellular CCR-3 surface receptor is provided under conditions to form a ligand-receptor complex, and the ligand-receptor complex is internalized into the cell. The internalized complex may alter a cellular function, such as cell proliferation, cell viability, chemotaxis, activation, trafficking, and/or preventing subsequent ligand binding. The ligand may have a compound bound to it, such as a toxin, a drug, an enzyme and/or a radionuclide, and the compound may be activated intracellularly. The compound may be bound to the ligand in a variety of ways, such as covalently or noncovalently, or a protein compound may be generated as a fusion protein with said ligand. The ligand may be eotaxin, eotaxin-2, RANTES, monocyte chemoattractant protein (MCP)-2, MCP-3 and/or MCP-4. The cell may be an eosinophil, a basophil, a lymphocyte and/or a microglial cell.

The invention is also directed to a composition for treating an eosinophil-mediated disorder. The composition is a ligand for a CCR-3 eosinophil receptor containing a compound such as a leukotriene inhibitor and/or an apoptosis inducer in a pharmaceutically acceptable formulation. The composition may be used to treat eosinophil-mediated disorders such as allergies, asthma, eczema, eosinophilic cardiomyopathy, eosinophilic gastroenteritis, hypereosinophilic syndrome, graft versus host disease, chronic fibrosis, a parasitic inflammatory disorder, drug reaction, eosinophilic pneumonias, episodic angioedema with eosinophilia, inflammatory bowel disease, eosinophilic leukemia and/or food enteropathy. The compound may be a prodrug that is activated upon internalization into the eosinophil.

The invention is further directed to a method to prevent eosinophilia by providing a ligand for a CCR-3 receptor on an eosinophil under conditions to form a ligand-receptor complex and internalizing the complex into an eosinophil. The method may have a compound bound to the ligand, such as a toxin, a drug, an enzyme, a leukotriene inhibitor, and/or an apoptosis inducer, and may be activated upon internalization into the eosinophil.

The invention is still further directed to a method to treat or protect against a human immunodeficiency virus (HIV). A ligand for a CCR-3 cell surface receptor is provided in a pharmaceutically acceptable formulation and under conditions to form a ligand-CCR-3 complex. HIV binding to the CCR-3 is prevented by internalizing the ligand-CCR-3 complex.

The invention is additionally directed to a method for down-regulating a CCR-3 cell surface receptor. A ligand for the receptor is provided under ligand-binding conditions, the ligand is bound to the receptor and the ligand and receptor are internalized into the cell. The ligand may be a chemokine, a chemokine analog, a small molecule antagonist and/or a small molecule agonist and may have a compound bound to the ligand.

One advantage of the invention includes the ability to prevent systemic drug toxicity by administering an drug that is activated intracellularly. These and other advantages will be apparent in light of the following figures and detailed description.

DETAILED DESCRIPTION OF THE PREFERRED EMBODIMENT

Figure 1:
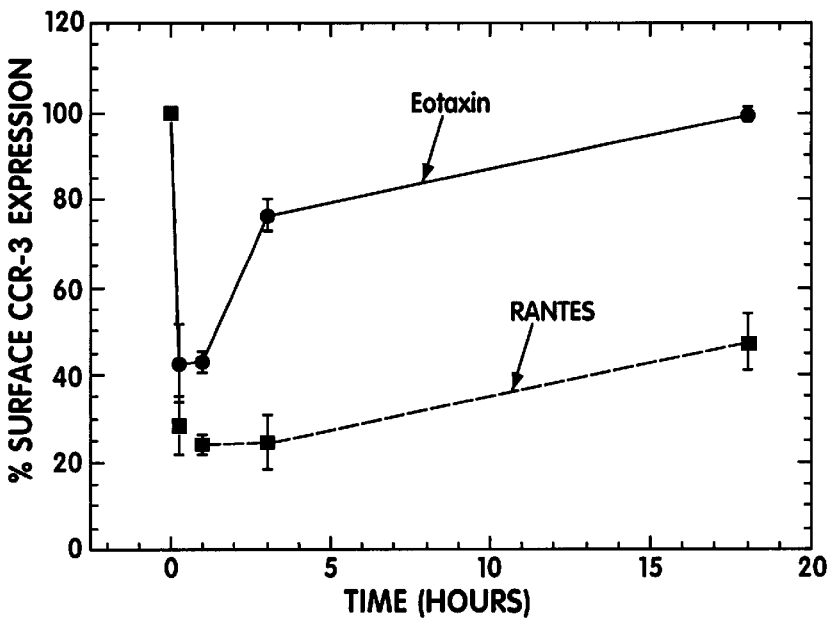
FIG. 1 is a graph showing CC chemokine receptor-3 (CCR-3) cell surface expression after stimulation of human eosinophils with CCR-3 ligands.

Chemokines are chemoattractants that orchestrate eosinophil accumulation in tissues and also induce cellular activation. Chemokines are grouped into subfamilies labeled CXC, CC, C and $CX_3C$ on the basis of the arrangement of their conserved cysteine residues. CXC chemokines are active on neutrophils, while CC chemokines have variable potencies for monocytes, lymphocytes, eosinophils and basophils. Eotaxin, disclosed in a co-pending U.S. application Ser. No. 08/522,713 entitled Eotaxin: An Eosinophil Chemoattractant, by Luster et al., and incorporated herein by reference in its entirety, is a chemokine that is the most selective eosinophil chemoattractant identified to date, and is responsible for eosinophil trafficking under normal conditions and during inflammatory processes.

The specific effects of chemokines are mediated by a family of seven transmembrane-spanning G-protein coupled receptors (GPCR). Seventeen of these chemokine receptors have been described: $CX_3CR-1$, XCR-1, CXCR-1 through 5, and CCR-1 through 10. CC chemokine receptor-3 (CCR-3) is the major chemokine receptor in eosinophils. CCR-3 appears to play a central role in allergic responses, since it is not only expressed on eosinophils but also on other cells that are central in allergic responses, namely, basophils and $T_H2$ lymphocytes. It binds multiple ligands, defined as a protein molecule that binds to another molecule, which include the polypeptides eotaxin-1 (eotaxin) and eotaxin-2, RANTES (regulated upon activation normal T-cell expressed and secreted), monocyte chemotactic protein (MCP)-2, MCP-3, and MCP-4. Of these chemokines, only eotaxin signals exclusively through CCR-3 receptors. Thus, expression and modulation of CCR-3 is a useful tool in assessing eosinophil targeting.

The finding that chemokines induce CCR-3 to undergo significant and prolonged receptor internalization has mechanistic implications for understanding eosinophil movement from one location to another ("trafficking") in vivo. It is widely accepted that chemokines induce cellular activation and chemoattraction. However, it is unclear if chemokines are also involved in stopping leukocyte movement. Eotaxin, which is expressed in the gastrointestinal tract, has been demonstrated to be required for the maintenance of gastrointestinal eosinophils at baseline (Matthews, A. N. et al. (1998) Proc. Natl. Acad. Sci. USA 95, 6273–6278). If eotaxin also induces receptor internalization with subsequent cellular hypo-responsiveness, then eosinophils would likely home into the intestine and become localized there since they would no longer be responsive to other chemokine gradients operating through CCR-3. In contrast, eosinophils in hematopoietic tissues or organs that do not express eotaxin, would remain responsive to the induction of subsequent chemokine gradients. Additionally, the observed inefficiency of receptor recycling following ligand binding, especially for RANTES, may have mechanistic implications concerning the difficulty in expressing CCR-3 on the surface of transfected cell lines. In one study, only 2–5% of CCR-3 transfected cells expressed CCR-3 on their surface even though substantial intracellular protein could be detected in most transfected cells (Ponath, P. D. et al. (1996) J. Exp. Med. 183, 2437–2448). This suggested a problem with CCR-3 protein trafficking. As yet another example, eotaxin may block cellular entry of CCR-3 trophic human immunodeficiency virus-1 (HIV-1) strains. Besides directly blocking HIV binding to CCR-3, eotaxin may inhibit HIV uptake by causing internalization of the CCR-3 co-receptor. This may be useful in studies of HIV in brain, for example in brain microglial cells.

The CCR-3 ligand may further contain a compound which is desirably targeted into the cell. The compound may be, in general, a toxin, a radionuclide, an enzyme, and/or combinations of these. Specifically, a toxin may be, for example, diphtheria toxin, Pseudomonas toxin, *Escherichia coli* toxin, cholera toxin, plant toxins such as ricin and sarcin, saponin, calicheamicin and so on. A drug may be, for example, a chemotherapeutic agent such as vincristine or cyclophosphamide. A radionuclide may be, for example, iodine $(I)^{131}$, $I^{125}$, or $indium^{111}$. An enzyme may be a herpes simplex kinase which would sensitize the cells to gancyclovir or another antiviral drug. The compound may inhibit a specific biochemical intracellular process such as leukotriene synthesis or cell viability. Inhibitors may be, for example, a leukotriene inhibitor such as a 5-lipoxygenase inhibitor (Zileuntin®), an apoptosis inducer such as tumor necrosis factor receptor associated factor (TRAF), receptor interacting protective (RIP), a protein synthesis inhibitor, a cell cycle inhibitor, etc. The compound may require cellular activation such as a prodrug, and may be administered in an inactive form and become activated only upon internalization in the cell. This would limit systemic toxicity due to non-specific binding of the toxin to cells that do not contain the CCR-3 receptor.

The compound may be attached to the ligand in a variety of ways whereby binding of the ligand to CCR-3 is not prevented. If the compound is a protein, a fusion protein of the ligand and compound may be generated using recombinant DNA wherein the nucleotide and/or amino acid sequence of ligand and compound are provided, as known to one skilled in the art. For example, the nucleotide sequence of the eotaxin ligand is disclosed in the aforementioned co-pending application Ser. No. 08/522,713, which has been incorporated by reference and may be used to create an eotaxin-compound fusion protein. Alternatively, a protein or non-protein compound may be bound to the ligand covalently, for example, using an amide linkage. The compound may also be bound by other types of interactions such as ionic bonds, hydrogen bonds, etc. The type of binding and the binding site or sites on the ligand may vary, as long as ligand binding to the receptor is not prevented.

The present results have several biological implications, especially since CCR-3 events have been investigated specifically in eosinophils. Conclusions concerning eosinophil chemokine receptor events have often been drawn from investigation of heterologous cell lines transfected with CCR-3. Since individual cell types often utilize distinct signaling events, it was important to examine chemokine triggered biochemical events in eosinophils. For example, formylmethionylleucylphenylalanine (fMLP) inhibits adenylate cyclase in fMLP receptor transfected cells, but not in human neutrophils (Uhing, R. J. et al. (1992) Biochem. Biophys. Res. Commun. 183, 1033–1039). In the following example, all experiments were thus performed in eosinophilic cells. However, since the CCR-3 is also expressed on other leukocytes such as basophils and lymphocytes, and on non-leukocytic cells such as brain microglial cells, the results may also have application to regulation of non-eosinophilic cells.

The invention has applications for the treatment of a variety of eosinophil-mediated disorders. These disorders include, but are not limited to, allergies including asthma, hay fever, uticaria, eczema, favism, arachnidism, insect bites and wasp stings, reactions to foreign proteins and angioneurotic edema, eosinophilic cardiomyopathy, eosinophilic gastroenteritis, hypereosinophilic syndrome, graft versus host disease, chronic fibrosis, parasitic inflammatory disorders such as trichinosis, visceral larva migrans and strongyloidiosis, drug reactions, eosinophilic pneumonias, episodic angioedema with eosinophilia, inflammatory bowel disease, diseases of blood forming organs such as chronic granulocytic leukemia, eosinophilic leukemia, polycythemia vera, heavy chain disease, after splenectomy, collagen diseases such as polyarteritis and lupus erythematosus, food enteropathy, skin diseases such as dermatitis, psoriasis, pemphigus, scabies and erythema multiforme, and so on. The composition of the invention may be administered in a pharmaceutically acceptable formulation by a variety of methods. Methods include parenteral administration, enteral administration either orally or rectally, transdermal administration, topical administration, inhalation either to the lungs or nasal mucosa, and so on.

The invention may also be useful in decreasing the activity of one or more biochemical processes ("down-regulation") by ligand internalization, thereby preventing subsequent ligand binding to the receptor. The ligand may be one or more of a chemokine, a chemokine analog, a small molecule (less than about 100–2000 daltons), eotaxin antagonist, a small molecule eotaxin agonist, and so on.

The experimental details and results are described in the following Example.

EXAMPLE

Eosinophil Purification

Eosinophils were purified from healthy or mildly atopic volunteers by negative immunomagnetic selection based on the method of Hansel et al., J. Immunol. Meth. 145, 105–110, 1991). Briefly, granulocytes were isolated from heparin-anticoagulated whole blood by dextran-sedimentation, Percoll centrifugation and hypotonic lysis of red blood cells. Cells were resuspended in Hank's buffered salt solution (BSS, Gibco BRL) with 2% FCS and incubated with 0.75 $\mu l/10^6$ cells anti-CD16 conjugated microbeads (MACS; Miltenyi Biotech Inc., Sunnyvale, Calif.) for 30 minutes at 4° C. The cell suspension was then applied onto a CS MACS (Miltenyl Biotech Inc.) column, and negative populations were collected through a magnetic field. The isolates routinely contained greater than 95% eosinophils with viability greater than 95% as assessed by Trypan blue exclusion. For internalization experiments, freshly isolated eosinophils were plated at $0.5 \times 10^6$/ml in medium supplemented with 50 pM IL-5. Cells were cultured (37° C., 5% $CO_2$) for a maximum of 22 hours and viability was greater than 95%.

Intracellular [$Ca^{2+}$] Measurement

Cells ($2 \times 10^6$/ml) were loaded with 5 $\mu M$ Fura-2 AM (Molecular Probes, Eugene, Oreg.) in HBSS with 1% FCS for 60 minutes at 37° C. in the dark. After two washes in flux buffer (145 mM NaCl, 4 mM KCl, 1 mM $NaHPO_4$, 0.8 mM $MgCl_2$, 1.8 mM $CaCl_2$, 25 mM Hepes and 22 mM glucose), cells were resuspended at $2 \times 10^6$ cells/ml and maintained on ice. Cells (2 ml) were prewarmed to 37° C. and stimulated in a cuvette with a continuously stirring magnetic bar using a RatioMaster fluorimeter (Photon Technology, Inc., South Brunswick, N.J.). Data were recorded as the relative ratio of fluorescence emitted at 510 nm after excitation at 340 nm and 380 nm (y axis) over time (x axis).

Flow Cytometry

Cells ($5 \times 10^5$) were washed with FACS-buffer (2% bovine serum albumin (BSA), 0.1% Na azide in PBS) and incubated with 0.5 $\mu g$ anti-hCCR-3 antibody (clone 7B11, kindly provided by Dr. Paul Ponath, Leukosite, Cambridge, Mass.), 0.5 $\mu g$ anti-CD18 antibody (clone TS1/18, ATCC) or the mouse isotype-matched control IgG2a or IgG1, respectively (Pharmingen, San Diego, Calif.) for 30 minutes at 4° C. After two washes in FACS-buffer, cells were incubated with 0.5 $\mu g$ FITC-conjugated isotype specific secondary antibody (Pharmingen) for 30 minutes at 4° C. in the dark. After two washes, labeled cells were subjected to flow-cytometry on a FACScan flow cytometer (Becton Dickinson) and analyzed using CELLQuest software (Becton Dickinson). Internalization of surface CCR-3 was assayed by incubating cells at 37° C. for indicated lengths of time with 0–1000 ng/ml human eotaxin or human RANTES (Peprotech, Rocky Hill, N.J.). In other experiments, eosinophils were exposed to pertussis toxin (List Laboratories, Campbell, Calif.) at a dose of 20–1000 ng/ml for three hours and chemokine was added for the last hour of the incubation period. In other experiments, eosinophils were exposed to 1–100 ng/ml of staurosporine (Sigma) for 3 hours and chemokine or phorbol 12-myristate 13-acetate (PMA, Sigma) was added for the last hour of the three-hour incubation period. Following chemokine exposure, cells were immediately placed on ice and washed with at least twice the volume of cold FACS buffer. Receptor density (%) was calculated as 100×(mean channel fluorescence [chemokine]−mean channel fluorescence [isotype-matched control])/(mean channel fluorescence [medium]−mean channel fluorescence [isotype-matched control]). Results were expressed as mean±standard error of the mean.

Western Blotting

Whole cell lysates were prepared from eosinophils by washing eosinophils twice in cold PBS and lysing in RIPA buffer (1% Nonidet P-40, 0.5% sodium deoxycholate and 0.1% sodium dodecyl sulfate (SDS) in PBS) with 10 $\mu g$/ml aprotinin, 10 $\mu g$/ml antipain, 10 $\mu g$/ml chymostatin, 10 $\mu g$/ml leupeptin, 10 $\mu g$/ml pepstatin A (all from Boehringer Mannheim) and 2 mM phenylmethyl sulfonyl fluoride (PMSF) (Sigma). Detergent insoluble material was removed by centrifugation at 12,000 g for 15 minutes at 4° C. Supernatants were stored in siliconized tubes and either used immediately or stored at −80° C. The protein concentration was determined using bicincholic acid assay (Pierce Chem Co., Rockford, Ill.) and 50 $\mu g$ protein was separated by electrophoresis on a 10% SDS-PAGE gel and transferred to a nitrocellulose membrane. Equal loading was verified by staining with PonceauS (Sigma). After blocking the membrane for 1 hour at room temperature in Tris-buffered saline with 0.2% Tween 20 (TBST) with 5% dry milk, the anti-CCR-3 polyclonal rabbit antiserum (kindly provided by Dr. Bruce Daugherty, Merck Research Laboratories, Rahway, N.J.) was added for 1 hour at room temperature (1:5,000 in TBST), followed by goat anti-rabbit horseradish peroxidase (HRP) conjugated secondary antibody (1:10,000 in TBST, Calbiochem, San Diego, Calif.). The signal was developed using enhanced chemiluminescence (Amersham, Arlington Heights, Ill.) according to the manufacturer's instructions. Antibody specificity was determined on lysates obtained from HOS.CD4 cells transfected with CCR-1 or CCR-3 (AIDS Research and Reference Reagent Program, Rockville, Md.). Cycloheximide (Sigma) was used at 10 µg/ml for 3 hours. Inhibition of protein synthesis (greater than 80%) was verified by $^{35}$S-methionine incorporation for three hours in the presence or absence of cycloheximide. Protein was precipitated by trichloroacetic acid (TCA) and radioactivity was measured in a β-scintillation counter.

Confocal Microscopy

Eosinophils were cultured in six-well plates on glass coverslips. For experiments, the chemokine was added to the growth medium for 3 hours at 37° C. To stop the reaction, cells were placed on ice and fixed with 3% paraformaldehyde in PBS. The fixed cells were washed with PBS, quenched with 15 mM glycine in PBS and permeabilized with 0.2% saponin in permeabilization buffer (1% cold fish gelatin and 1% BSA in PBS). Staining was achieved with the 7B11 antibody (0.75 µg per coverslip) in 1% cold fish gelatin and 3% BSA in PBS for 1 hour at room temperature. Following three washes in 1% cold fish gelatin in PBS, Texas Red-conjugated anti-mouse IgG (Jackson Immunoresearch Laboratories, Inc., West Grove, Pa.) was added for one hour at room temperature. Cells were washed three times with 1% cold fish gelatin, twice with PBS and once with water. Coverslips were mounted onto slides, sealed and stored at −20° C. until analysis on a Leica DMIRBE inverted microscope equipped with a confocal laser scanner. Images were analyzed with Metamorph (Universal Imaging Corporation, West Chester, Pa.) and printed in Adobe Photoshop (Adobe Systems Inc., Mountain View, Calif.). In some experiments, fresh human eosinophils were treated with chemokine for 15 minutes, cytocentrifuged, and stained for CCR-3 as above.

Results

To determine if CCR-3 attenuation involved modulation of receptor expression, receptor internalization after ligand binding was examined on AML 14.3 D10 cells. This cell line is an immature eosinophilic myelocytic cell line that expressed high levels of functionally active CCR-3. The surface expression of CCR-3 over a time period of 18 h following exposure of eosinophils to eotaxin was investigated by fluorescence activated cell sorter (FACS) analysis. Freshly isolated peripheral blood eosinophils were cultured with 100 ng/ml eotaxin or RANTES, another CCR-3 ligand, for indicated lengths of time. Cell surface expression of CCR-3 was measured by FACS analysis and was compared to CCR-3 expression of eosinophils that had not been treated with the chemokine. The results are expressed as means±standard error of the mean (SEM) of three separate experiments. The results were statistically significant for all time points ($p<0.05$, paired Student's t-test).

As shown in FIG. 1, 100 ng/ml of eotaxin (solid line) resulted in loss of receptors. This loss was detectable after 15 min, remained reduced at 3 h and returned to baseline levels at 18 h. Only 43%±9%, 43%±2%, and 76%±4% of the original receptor level was present on the eosinophil surface after 15 min, 1 h, and 3 h, respectively. Also as shown in FIG. 1, exposure of eosinophils to 100 ng/ml RANTES (dashed line), also internalized CCR-3. In this experiment only 29%±6%, 24%±2%, 24%±6%, and 47%±7% of the original receptor level was present on the surface after 15 min, 1 h, 3 h, and 18 h, respectively.

FIGS. 2A–H show results from a representative experiment (number of experiments (n)=3) for treatment with both eotaxin and RANTES. Eosinophils were incubated with either eotaxin (FIGS. 2A–D) or RANTES (FIGS. 2E–H) for 15 min (A,E), 1 h (B,F), 3 h (C,G) and 18 h (D,H). Cell surface expression was assessed by FACS analysis. The isotype-matched control is shown as the filled graphs, the CCR-3 expression without chemokine (eotaxin or RANTES) is shown as a solid line, and the CCR-3 expression with chemokine (eotaxin or RANTES) is shown as a dashed line. In all instances, RANTES binding to CCR-3 induced a greater magnitude of CCR-3 internalization and with a longer duration than with eotaxin binding to CCR-3 ($p<0.05$).

To determine if the difference in CCR-3 internalization quantity and duration between RANTES and eotaxin could be related to different potencies of these two chemokines, several doses of both chemokines were analyzed. Peripheral blood eosinophils were cultured with either eotaxin or RANTES for 3 h or 18 h. Cell surface expression of CCR-3 was measured by FACS analysis and compared to CCR-3 expression of eosinophils not treated with the chemokine.

Figure 3A:
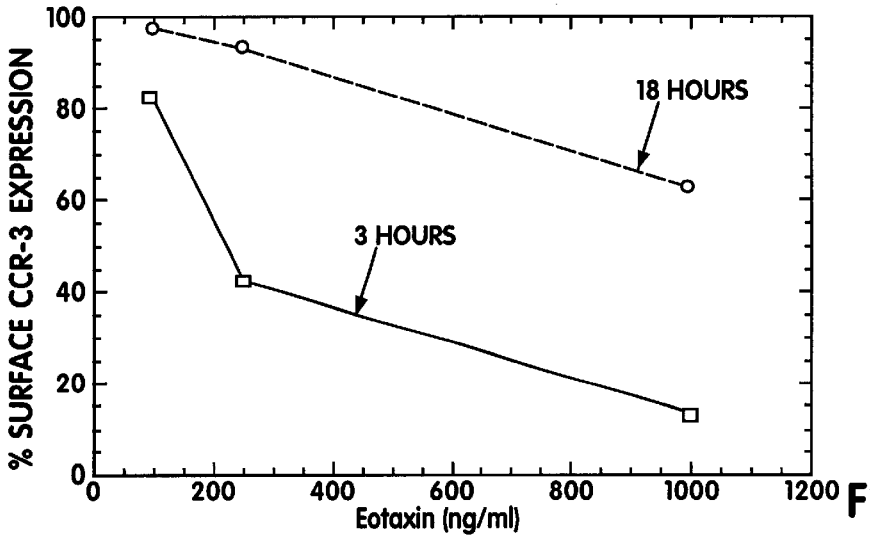
FIGS. 3A–B are graphs showing dose-dependent ligand-induced CCR-3 internalization on eosinophils.
Figure 3B:
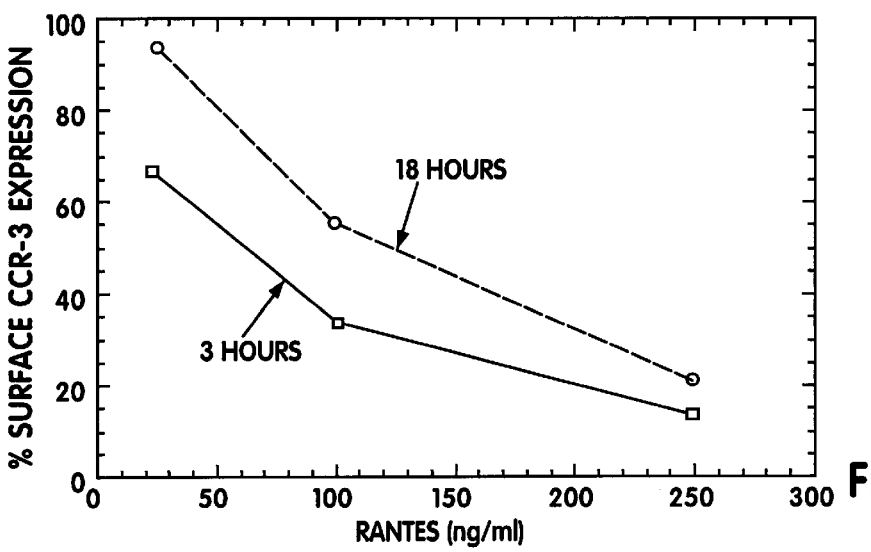
Figure 2A:
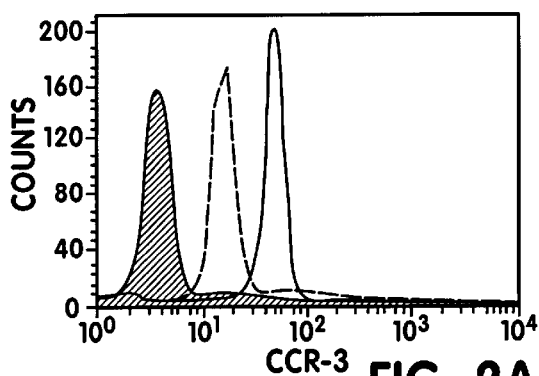
FIGS. 2A–H are graphs showing CCR-3 cell surface expression after stimulation with eotaxin or RANTES.
Figure 2E:
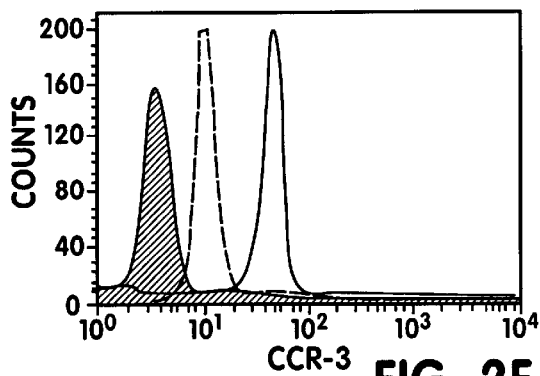
Figure 2B:
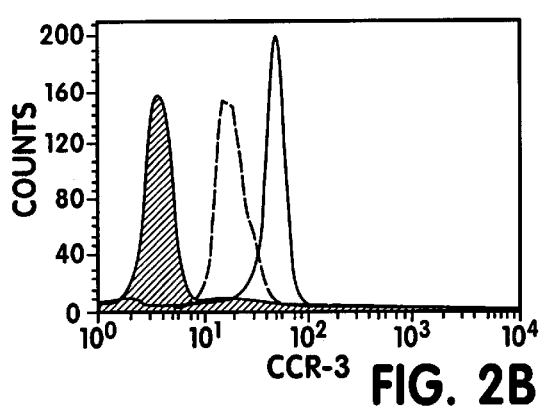
Figure 2F:
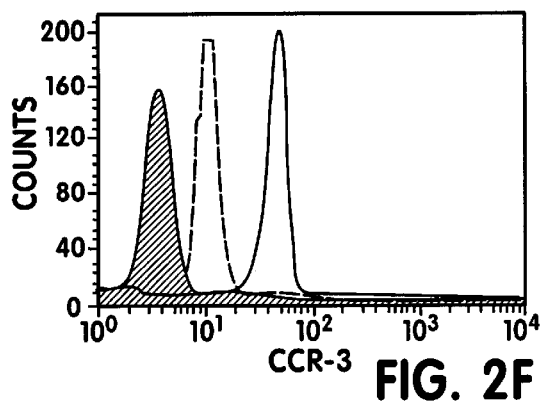
Figure 2C:
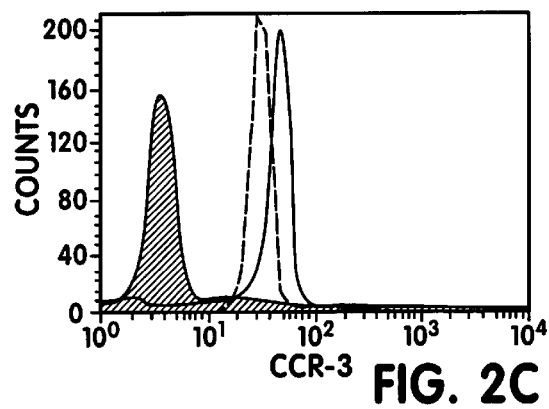
Figure 2G:
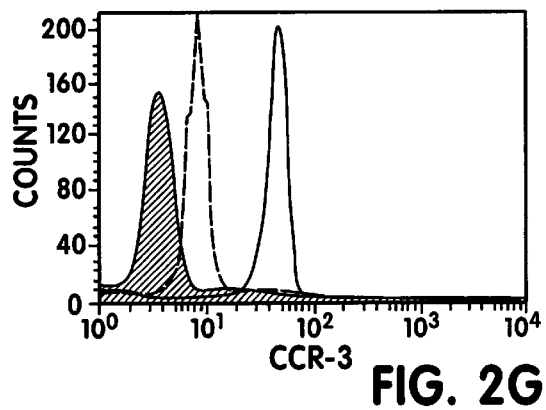
Figure 2D:
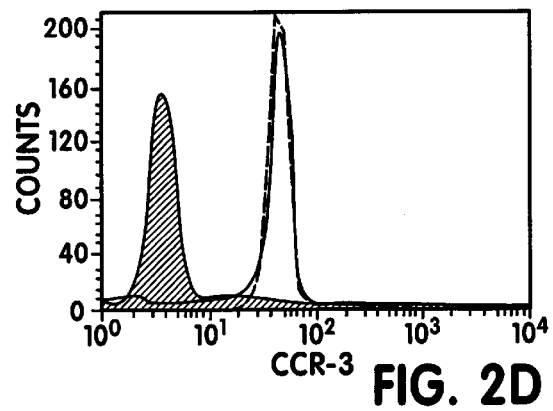
Figure 2H:
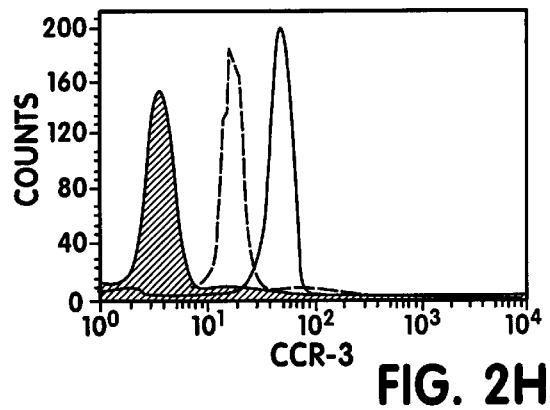

As shown in FIG. 3, there was a dose-dependent internalization of CCR-3 in eosinophils cultured either with eotaxin (FIG. 3A) or RANTES (FIG. 3B) for 3 h (solid line) or 18 h (dashed line). At all doses, eotaxin was less potent than RANTES. At the highest dose of eotaxin tested (1000 µg/ml), there was still reduction in CCR-3 surfaces expression at 18 h. A lower dose of RANTES, 100–250 ng/ml, also demonstrated reduction in CCR-3 surface expression at 18 h.

The effect of chemokine removal on surface expression of CCR-3 following receptor internalization was investigated. Eosinophils were exposed to eotaxin or RANTES for 15 min, washed extensively (more than two times) to remove chemokine, and then monitored for CCR-3 expression over the next two hours. After exposure to eotaxin, CCR-3 expression was 49% at 0 min, 43% at 30 min, 47% at 60 min, and 88% at 120 min. After exposure to RANTES, CCR-3 expression was 37% at 0 min, 33% at 30 min, 42% at 60 min, and 86% at 120 min (n=2 or 3) for each time point and for each chemokine.

To verify that ligand binding alone was insufficient to produce the demonstrated reduced CCR-3 expression, eosinophils were exposed to chemokine at 4° C. followed by FACS analysis. A temperature of 4° C. permitted ligand binding to CCR-3, but prevented CCR-3 internalization. The results indicated that at 4° C. there was no internalization of surface CCR-3, whereas replicate cells that had been exposed to the cytokine at 37° C. demonstrated receptor internalization (n=2, data not shown). Thus, ligand binding alone was not sufficient to decrease CCR-3 detection. Receptor internalization was specific for CCR-3, since the expression level of an unrelated cell surface molecule, CD18, did not change with eotaxin treatment (n=3, data not shown).

Confocal microscopy was performed to demonstrate CCR-3 ligand-induced receptor internalization. Experiments were also conducted with fresh human eosinophils to verify that ligand-induced receptor internalization, rather than antigen blocking of the receptor by chemokine, was occurring. These experiments revealed translocation of CCR-3 staining predominantly from a membrane-associated pattern to a granular pattern in a perinuclear location, consistent with endosomes (data not shown).

Since internalization of CCR-3 may induce degradation of the receptor, the level of CCR-3 protein was analyzed by Western blot analysis. The conditions for Western blot analysis were first established from control cells which were either human eosinophils, untransfected HOS.CD4 cells, or HOS.CD4 cells transfected with CCR-1 or CCR-3. Whole cell lysates (50 µg) were electrophoresed in a 10% sodium dodecyl sulfate-polyacrylamide gel, transferred to nitrocellulose, and stained with the polyclonal anti-CCR-3 antibody. The results are representative of three separate experiments. Molecular weight standards are shown on the side of each of FIGS. 4A–C.

Figure 4A:
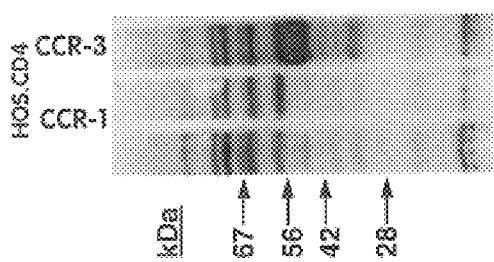
FIG. 4A is a Western blot analysis showing CCR-3 expression in HOS.CD4 cells transfected with CCR-1 or CCR-3.
Figure 4B:
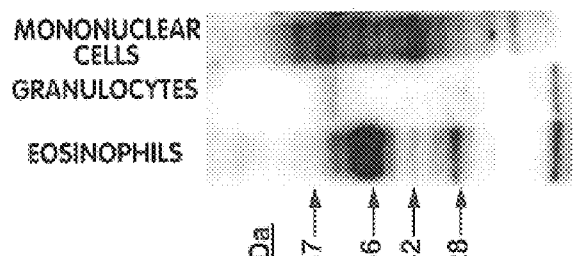
FIG. 4B is a Western blot analysis showing CCR-3 expression in peripheral blood leukocytes.
Figure 4C:
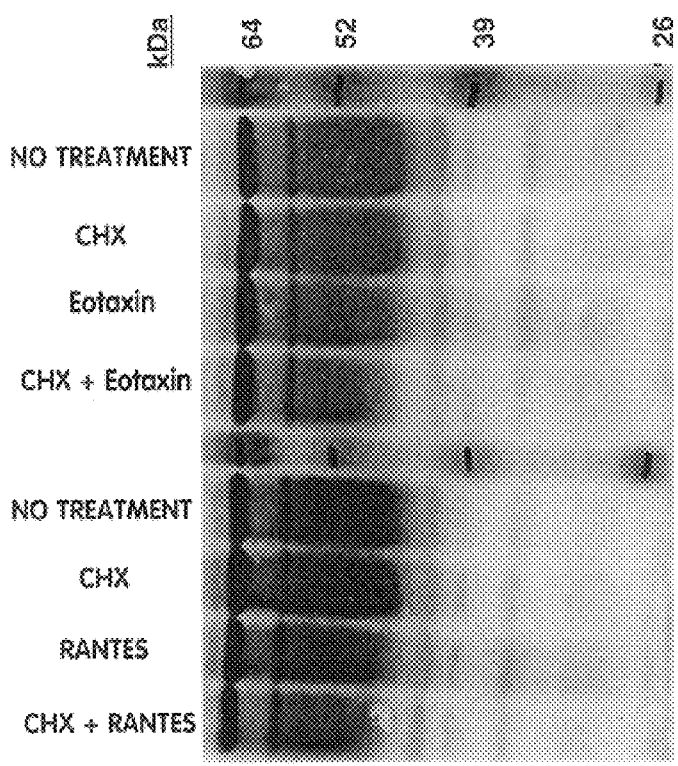
FIG. 4C is a Western blot analysis for CCR-3 showing treatment of eosinophils with chemokines in the presence or absence of cycloheximide.

As shown in FIG. 4A, and using polyclonal rabbit anti-human CCR-3 serum, the HOS.CD4 cells transfected with CCR-3 showed a strong, large band between molecular weight 50–60 kDa. This band was absent in HOS.CD4 cells transfected with CCR-1. As shown in FIG. 4B, human eosinophils had a strong band between 50–60 kDa, but this band was absent in non-eosinophilic granulocytes or mononuclear cells. In all cases, detection of immunoreactive CCR-3 protein was lost if the protein extract was boiled prior to electrophoresis.

Figure 5A:
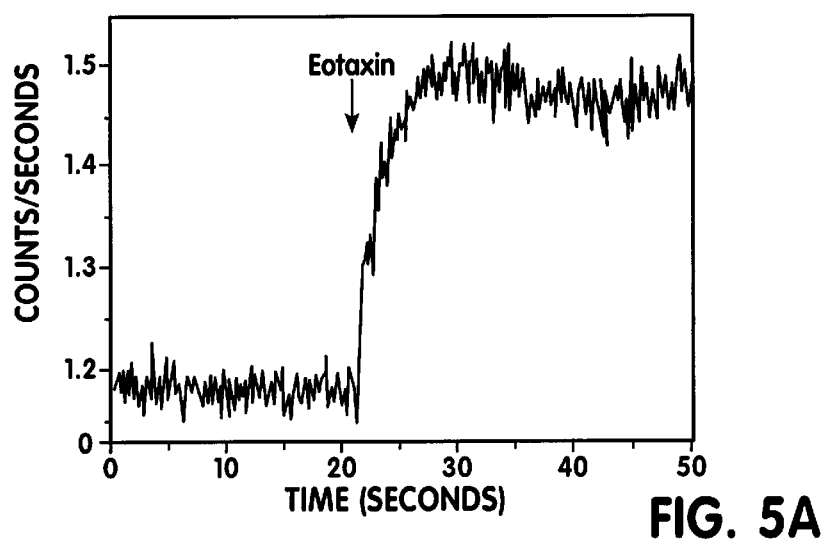
FIGS. 5A–D are graphs showing the effect of pertussis toxin on ligand-induced calcium flux and CCR-3 internalization.
Figure 5B:
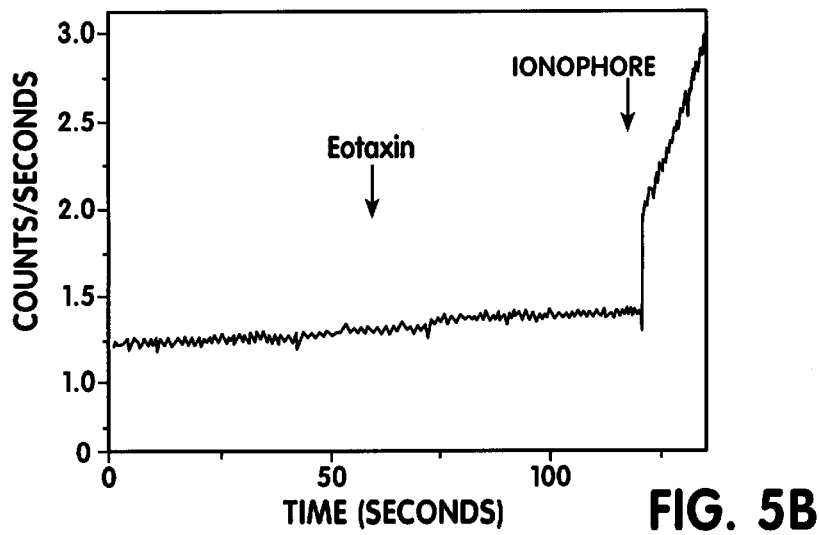
Figure 5C:
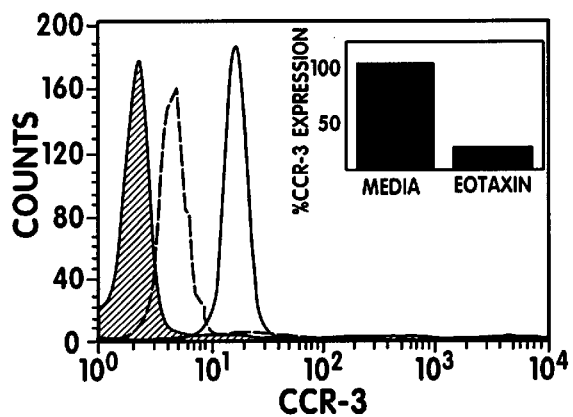

Human eosinophils were also treated with media alone or medium containing eotaxin (250 ng/ml) or RANTES (100 ng/ml) for three hours. These conditions promote optimal chemokine-induced receptor internalization. As shown in FIG. 5C, Western blot analysis of whole cell lysates revealed that the level of CCR-3 protein decreased by about 30%. This decreased level of CCR-3 was further reduced by about 60% when eosinophils were treated with cycloheximide (CHX) for the three hour cytokine exposure. Cells treated with cycloheximide alone showed no change in the level of immunoreactive CCR-3 protein compared with cells incubated in media alone. The antibody used in Western blot analysis recognizes the carboxy-terminal region of CCR-3, thus, the absence of degradation products may be due to the loss of this epitope in the degradation products. These experiments demonstrated that internalization of CCR-3 is accompanied by receptor degradation, and that de novo synthesis of CCR-3 protein is involved in maintaining the total level of CCR-3 protein following chemokine binding.

Figure 4D:
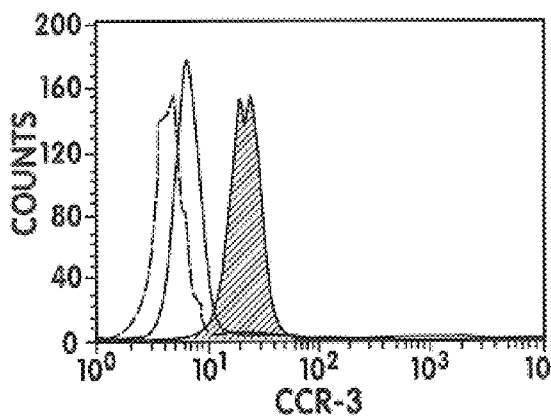
FIG. 4D is a graph showing cells treated with eotaxin in the presence or absence of cycloheximide.

To determine if re-expression of CCR-3 on the cell surface is dependent upon protein synthesis, CCR-3 expression on cells treated with eotaxin either in the presence or absence of cycloheximide was monitored by FACS analysis. The results are shown in FIG. 4D. Cells treated with eotaxin alone are shown with a solid line, cells treated with eotaxin plus cycloheximide are shown with a dashed line, and untreated cells are shown with the filled graph. Following treatment with 100 ng/ml eotaxin for three hours, the receptor was beginning to re-appear on the cell surface in the absence of cycloheximide. In contrast, in cells treated with eotaxin in the presence of cycloheximide, the receptor expression on the cell surface remained low. This indicated that chemokine treatment induced protein degradation and that new protein synthesis was involved in maintaining the level of CCR-3 protein following chemokine treatment.

Figure 5D:
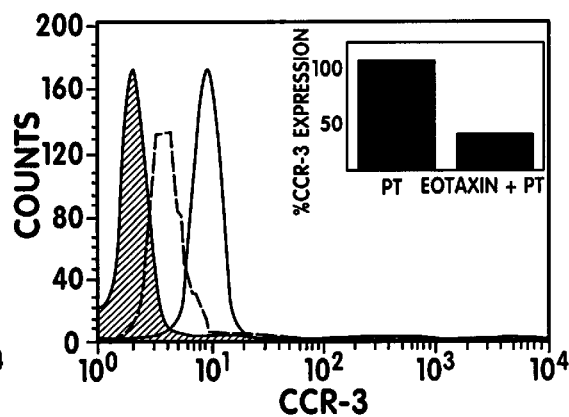

In elucidating the mechanism of CCR-3 internalization, it was of interest to determine if G-protein coupling was required. CCR-3 induced calcium transients are known to be inhibited by pertussis toxin, suggesting that CCR-3 couples to $G_i$-proteins. The dose of pertussis toxin that was able to completely inhibit eotaxin-induced calcium transients in eosinophils was first determined. Eosinophils were cultured for three hours in medium alone (FIG. 5A and FIG. 5C), or medium containing 20 ng/ml pertussis toxin (FIG. 5B and FIG. 5D). Calcium transients (FIG. 5A and FIG. 5B) induced by 500 ng/ml eotaxin treatment are shown. Data are presented as the relative ratio of fluorescence emitted at 510 nm after excitation at 340 nm and 380 nm (y axis) over time (x axis). Replicate cells were also exposed to eotaxin for the last one hour of the culture, and the level of CCR-3 expression was determined (FIG. 5C and FIG. 5D). Cell surface expression of CCR-3 was measured by FACS analysis and compared between cells treated with eotaxin (dashed line) and cells not treated with chemokine (solid line), with isotype matched control antibody expression indicated by the filled graph. The insets in FIG. 5C and FIG. 5D represent data expressed as a percentage of CCR-3 expression.

Treatment of eosinophils with 100–1000 ng/ml pertussis toxin for three hours inhibited calcium flux, and also reduced CCR-3 expression to 30% (data not shown). At a lower dose of 20 ng/ml pertussis toxin, inhibition of eotaxin-induced calcium transients was maintained, as shown in FIG. 5A and FIG. 5B, but the level of CCR-3 was not significantly reduced. As shown in FIG. 5C and FIG. 5D, exposure of eosinophils to 20 ng/ml of pertussis toxin did not block eotaxin-induced receptor internalization at a 100 ng/ml dose of eotaxin. There was also no evidence of an effect of pertussis toxin using eotaxin at 10 or 500 ng/ml (data not shown). These data indicated that CCR-3 internalization was not dependent upon $G_i$-protein coupling nor calcium transients in human eosinophils. Interestingly, high doses of pertussis toxin alone down-regulated the level of surface CCR-3 expression. The dissociation of G-protein coupling and GPCR internalization has been reported for other selected GPCR such as CXCR-4.

Figure 6A:
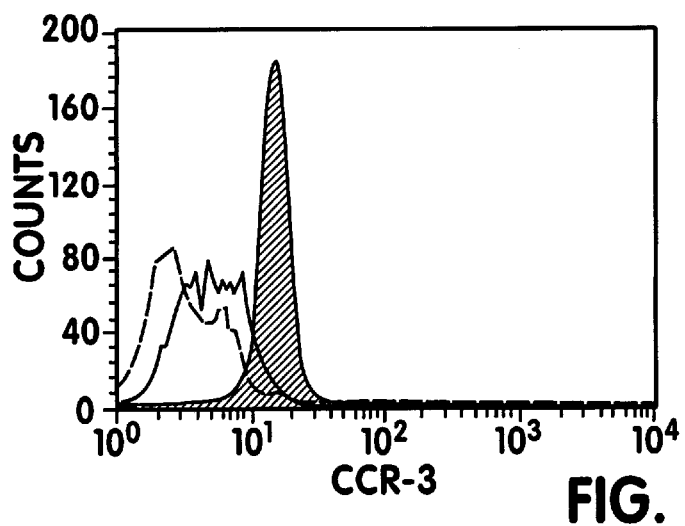
FIGS. 6A–C are graphs showing the involvement of protein kinase C in CCR-3 internalization.
Figure 6B:
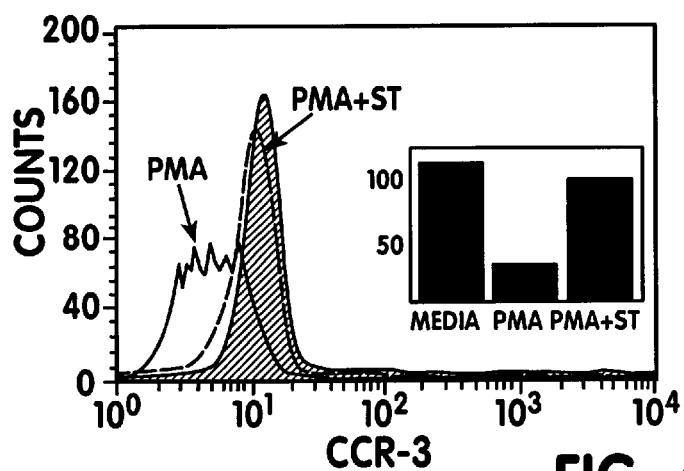
Figure 6C:
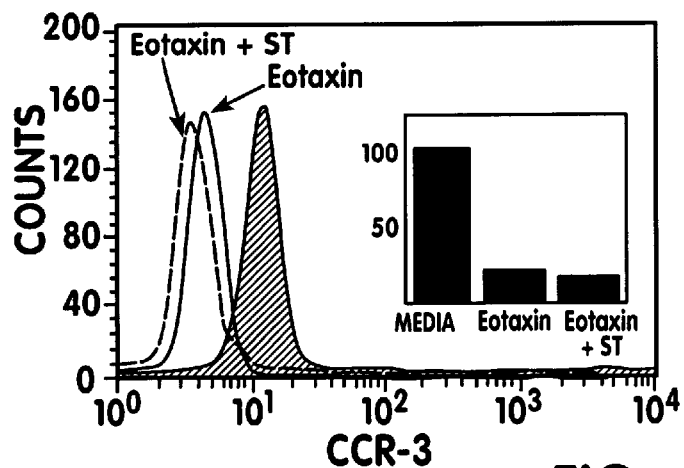

Since internalization of some GPCR is dependent upon protein kinase C (PKC), involvement of PKC in ligand-induced CCR-3 internalization was determined. With reference to FIGS. 6A–C, human eosinophils were treated with PMA to determine if pharmacological activation of PKC was able to cause down-regulation of CCR-3. Eosinophils were treated with increasing doses of 0.1 ng/ml PMA (dashed line), and the level of CCR-3 was analyzed by FACS analysis. As shown in FIG. 6A, treatment of eosinophils with PMA for one hour resulted in a dose-dependent down-modulation of CCR-3 surface expression. As shown in FIG. 6B, pretreatment of eosinophils for two hours with 10 ng/ml of staurosporine (ST) (dashed line), an inhibitor of PKC, prior to PMA treatment completely inhibited PMA-induced CCR-3 down modulation. The inset represents data expressed as a percentage of CCR-3 expression. At this dose, staurosporine had no effect on the level of eotaxin (100 ng/ml)-induced CCR-3 internalization. As shown in FIG. 6C, the eotaxin-induced reduction of CCR-3 surface expression (solid line) was not inhibited by 10 ng/ml staurosporine treatment (dashed line). The level of CCR-3 expression in untreated cells is shown by the filled graph. The inset represents data expressed as a percentage of CCR-3 expression. There was also no evidence of staurosporine effect at 10 or 500 ng/ml eotaxin (data not shown). These results indicated that although PMA induced down-modulation of CCR-3, PKC was not involved in the ligand-induced internalization of CCR-3. However, in these experiments CCR-3 down-modulation was induced by activation of PKC with PMA. Similarly, even though PMA and ligands induce rapid phosphorylation of CXCR-2, only PMA-induced phosphorylation is inhibited by staurosporine. These data indicate that at least two pathways exist for down-modulating CCR-3 expression: one mediated by PKC and another mediated by chemokines and independent of PKC. The latter pathway may be dependent upon G-protein related kinases, such as GRK-2, which has been shown to be involved in CCR-5 internalization (Aramori, I. et al. (1997) Embo J. 16, 4606, 4616).

Ligand-induced modulation of chemokine receptor expression has only been examined for a limited number of chemokine receptors and variable pathways have been reported. IL-8 induces rapid internalization of its receptor in neutrophils (Samanta, A. K. et al. (1990) J. Biol. Chem. 265, 183–189). Stromal-cell derived factor-1 α induces a decrease of cell surface CXCR-4 in the CEM T-cell line, HeLa cells and peripheral blood mononuclear cells (Amara, A. et al. (1997) J. Exp. Med. 186, 139–146, Forster, R. et al. (1998) J. Immunol. 160, 1522–1531). Additionally, CCR-5 ligands induce receptor internalization in lymphocytes, monocytes/macrophages and CCR-5 transfected CHO cells (Mack, M. et al. (1998) J. Exp. Med. 187, 1215–1224). In these cases, the receptors enter an endocytic pathway, but recycle by three hours after ligand binding. In contrast, CXCR-2 undergoes internalization and does not recycle since it enters a degradative lysosomal pathway (Mueller, S. G. et al. (1995) J. Biol. Chem. 270, 10439–10448). Rapid ligand-induced internalization of CCR-1 in transfected CHO cells (Solari, R. et al. (1997) J. Biol. Chem. 272, 9617–9620) and CCR-2B in transfected HEK-293 cells (Franci, C. et al. (1996) J. Immunol. 157, 5606–5612) have been described, but their intracellular processing was not studied. The diverse mechanisms of ligand induced modulation of chemokine receptors indicate the importance of dissecting these processes for each chemokine receptor.

Other variations or embodiments of the invention will also be apparent to one of ordinary skill in the art from the above description. For example, since the receptor is found on other cells, the invention may be used to inhibit the activity of these cells such as non-eosinophilic granulocytes (e.g., basophils) and mononuclear leukocytes (e.g., lymphocytes) as well as other cells. Thus, the forgoing embodiments are not to be construed as limiting the scope of the invention.

What is claimed is:

1. A method of intracellular targeting comprising providing a compound bound to a ligand for a CCR-3 surface receptor on a cell under conditions to form a ligand receptor complex and internalizing said complex into the cell.

2. The method of claim 1 wherein said internalized complex alters a function of said cell.

3. The method of claim 2 wherein the function is selected from the group consisting of proliferation, viability, chemotaxis, activation, trafficking, prevention of subsequent ligand binding and combinations thereof.

4. The method of claim 1 wherein said compound is selected from the group consisting of a toxin, a drug, an enzyme, a radionuclide, an inhibitor, and combinations thereof.

5. The method of claim 1 wherein said compound is covalently bound to said ligand.

6. The method of claim 1 wherein said compound is noncovalently bound to said ligand.

7. The method of claim 1 wherein said compound is generated as a fusion protein with said ligand.

8. The method of claim 1 wherein said compound is activated intracellularly.

9. The method of claim 8 wherein said compound is a prodrug.

10. The method of claim 1 wherein said ligand is selected from the group consisting of a chemokine, a chemokine analog, a small molecule antagonist, a small molecule agonist and combinations thereof.

11. The method of claim 10 wherein said chemokine is selected from the group consisting of eotaxin, eotaxin-2, RANTES, monocyte chemoattractant protein (MCP)-2, MCP-3, MCP-4 and combinations thereof.

12. The method of claim 1 wherein said cell is selected from the group consisting of an eosinophil, a basophil, a lymphocyte, a microglial cell and combinations thereof.

13. A composition for treating an eosinophil-mediated disorder comprising a ligand for a CCR-3 eosinophil receptor at a dose sufficient for internalization of said receptor and having a therapeutic compound bound to said ligand in a pharmaceutically acceptable formulation.

14. The composition of claim 13 wherein said compound is selected from the group consisting of a toxin, a drug, an enzyme, a radionuclide, an inhibitor and combinations thereof.

15. The composition of claim 14 wherein the inhibitor is selected from the group consisting of a leukotriene inhibitor, an apoptosis inducer and combinations thereof.

16. The composition of claim 13 wherein said disorder is selected from the group consisting of allergy, asthma, eczema, eosinophilic cardiomyopathy, eosinophilic gastroenteritis, eosinophilic leukemia, hypereosinophilic syndrome, graft versus host disease, chronic fibrosis, a parasitic inflammatory disorder, drug reaction, eosinophilic pneumonias, episodic angioedema with eosinophilia, inflammatory bowel disease, food enteropathy and combinations thereof.

17. The composition of claim 13 wherein said compound is a prodrug that is activated upon internalization into said eosinophil.

18. The composition of claim 13 administered by a method selected from the group consisting of parenteral, enteral, transdermal, topical, inhalation and combinations thereof.

19. A method to treat eosinophilia comprising providing a ligand for a CCR-3 receptor having a compound bound to said ligand on an eosinophil under conditions to form a ligand-receptor complex, and internalizing said complex into said eosinophil.

20. The method of claim 19 wherein said compound is selected from the group consisting of a toxin, a drug, an enzyme, an inhibitor and combinations thereof.

21. The method of claim 19 wherein said compound is activated upon internalization into said eosinophil.

22. The method of claim 19 wherein said providing is by administering by a method selected from the group consisting of parenteral, enteral, transdermal, topical, inhalation and combinations thereof.

23. A method for down-regulating a CCR-3 cell surface receptor comprising providing a ligand for said receptor under ligand-binding conditions, binding said ligand to said receptor and thereafter internalizing said receptor into said cell.

24. The method of claim 23 wherein said ligand is selected from the group consisting of a chemokine, a chemokine analog, a small molecule antagonist, a small molecule agonist and combinations thereof.

25. The method of claim 23 further comprising a compound bound to said ligand.

* * * * *

UNITED STATES PATENT AND TRADEMARK OFFICE
CERTIFICATE OF CORRECTION

PATENT NO. : 6,358,697 B2  
APPLICATION NO. : 09/296071  
DATED : March 19, 2002  
INVENTOR(S) : Marc E. Rothenberg Page 1 of 1

It is certified that error appears in the above-identified patent and that said Letters Patent is hereby corrected as shown below:

Please delete the following paragraph from the specification of the above-identified patent application:

Column 1, paragraph 1, lines 4 through 8:
"The U.S. Government has a paid-up license in this invention and the right in limited circumstances to require the patent owner to license others on reasonable terms as provided for by the terms of Grant No. R01-AI42242-02 awarded by the National Institutes of Health."

and insert therefore the following paragraph:

"This invention was made with Government support under Grant No. R01-AI042242, awarded by the National Institutes of Health. The Government has certain rights in this invention."

Signed and Sealed this
Twenty-first Day of June, 2011

David J. Kappos
*Director of the United States Patent and Trademark Office*